United States Patent
Garito et al.

(10) Patent No.: US 7,160,295 B1
(45) Date of Patent: Jan. 9, 2007

(54) FLEXIBLE ELECTROSURGICAL ELECTRODE FOR TREATING TISSUE

(76) Inventors: Jon C. Garito, 3333 Royal Ave., Oceanside, NY (US) 11572-3625; Alan G. Ellman, 3333 Royal Ave., Oceanside, NY (US) 11572-3625

( * ) Notice: Subject to any disclaimer, the term of this patent is extended or adjusted under 35 U.S.C. 154(b) by 299 days.

(21) Appl. No.: 10/914,740

(22) Filed: Aug. 9, 2004

Related U.S. Application Data

(63) Continuation-in-part of application No. 10/742,031, filed on Dec. 22, 2003, now abandoned.

(51) Int. Cl.
*A61B 18/14* (2006.01)
(52) U.S. Cl. .............................. 606/41; 606/45; 606/49
(58) Field of Classification Search ................ 606/41, 606/45, 49
See application file for complete search history.

(56) References Cited

U.S. PATENT DOCUMENTS

| | | | | |
|---|---|---|---|---|
| 2,102,270 | A * | 12/1937 | Hymas | 606/49 |
| 3,858,586 | A * | 1/1975 | Lessen | 606/49 |
| 4,103,688 | A * | 8/1978 | Edwards | 606/49 |
| 4,565,200 | A * | 1/1986 | Cosman | 600/373 |
| 5,047,026 | A * | 9/1991 | Rydell | 606/48 |
| 5,364,393 | A * | 11/1994 | Auth et al. | 606/34 |
| 5,437,664 | A * | 8/1995 | Cohen et al. | 606/42 |
| 6,607,528 | B1 * | 8/2003 | Quick et al. | 606/45 |

* cited by examiner

*Primary Examiner*—Lee S. Cohen

(57) ABSTRACT

A unipolar electrosurgical electrode or probe that is configured for use in MIS electrosurgical procedures. The electrosurgical electrode comprises a long, thin, flexible, insulated wire configured to cooperate with the small cannula of a mini-endoscope to reach interior tissue not normally reachable by electrosurgical electrodes. When energized, a unipolar discharge is generated at the working end of the electrode. The probe can be used for spinal and endonasal procedures.

10 Claims, 3 Drawing Sheets

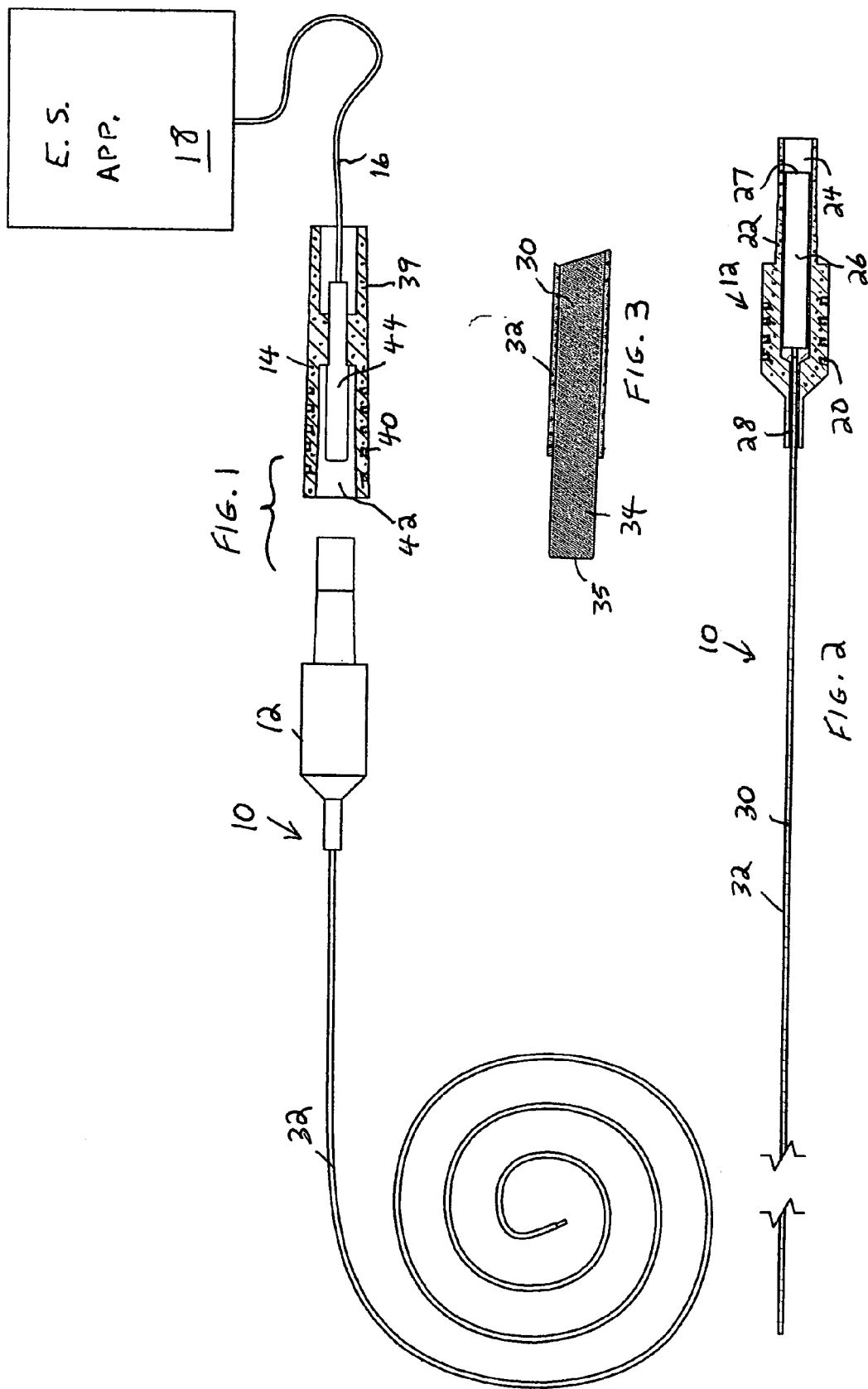

FLEXIBLE ELECTROSURGICAL ELECTRODE FOR TREATING TISSUE

RELATED APPLICATION

This application is a CONTINUATION-IN-PART of a commonly owned patent application Ser. No. 10/742,031, filed in the U.S. Patent And Trademark Office on Dec. 22, 2003, now abandoned, and entitled FLEXIBLE ELECTROSURGICAL ELECTRODE FOR TREATING TISSUE This invention relates to an electrosurgical probe for treating ailments or diseases by minimally invasive surgery (MIS) or similar procedures.

BACKGROUND OF THE INVENTION

Our prior patent, U.S. Pat. No. 5,505,728, whose contents are incorporated herein by reference, describes a novel electrosurgical electrode for ablating or shrinking throat tissue in a surgical procedure. This is accomplished by an electrosurgical electrode activated by electrosurgical currents that is applied by the surgeon to the patient.

Our prior patent, U.S. Pat. No. 6,447,510, whose contents are incorporated herein by reference, describes a novel electrosurgical electrode for the treatment of benign and malignant lesions of the upper aerodigestive tract. This is accomplished by an electrosurgical electrode activated by electrosurgical currents and configured such that it can be applied by the surgeon to the patient via the rigid cannula of a laryngo-pharyngoscope. The electrode is stiff and specifically configured for this particular procedure.

There is a need in the art for devices to simplify the treatment by MIS of other tissues which cannot be reached by the electrodes described in the referenced patents. These include, among others, epidural scar tissue, adhesions and other pathology, spinal diseases such as intradiscal shrinkage or ablation, endoscopic endonasal procedures, as well as treating internal tissues reachable only by, for example, being snaked or threaded up into a vein to travel up to leg lesions, etc.

Laser have been used for some of such purposes in a MIS procedure but has disadvantages, which include, but are not limited to: the radiation can be dangerously reflected by shiny reflecting metallic surfaces, requiring the use of non-reflective working channel scopes, and limiting the use of reflecting instruments; laser beam scatter may cause skin burns, fire or the generation of toxic products; problems may arise if the laser beam impinges on the cannula or other equipment; safety measures are necessary such as warning lights, safety glasses, and laser safety courses are required.

SUMMARY OF THE INVENTION

An object of the invention is an improved electrosurgical probe for treating tissue.

Another object of the invention is an improved electrosurgical probe for treating tissue that can use a standard operating room working channel fiberoptic scope or endoscope.

Still another object of the invention is an improved electrosurgical probe that can be used with flexible steerable endoscopes.

Still another object of the invention is an improved electrosurgical probe for treating tissue that has in the past been reachable and treatable only through the use of laser radiation.

In accordance with a feature of the invention, an electrosurgical probe comprises a very long, thin, flexible, insulated, monopolar wire electrode, so thin and flexible that it can be used with a miniature or micro-sized endoscope combining imaging optics and an instrument channel with an overall diameter below about 3 mm. It is also sufficiently thin and flexible, but also stiff enough, that it can be used with flexible steerable endoscopes and in addition can be snaked down or threaded up into a vein to reach leg lesions. Because of its capability of use with a miniature or micro-sized endoscope in a standard operating environment, hospital or office, it allows a surgeon to conduct a procedure with improved visualization of the surgical site. With the preferred dimensions given below, a 600 mm electrode can easily be coiled without breaking to form a 3-turn loop with a diameter as little as 2–3 inches.

In a preferred embodiment, the elongated probe comprises at its proximal end a novel connector, connected by cable to a standard electrosurgical apparatus or its equivalent, and that can be made sterile and thus operable by the surgeon with fingers of only one hand, allowing the surgeon to remove the electrosurgical probe of the invention and attach another electrode to perform another function at the same surgical site all while maintaining a sterile field at the patient's side.

In another preferred embodiment, the elongated probe comprises at its distal end an exposed blunt wire end.

In still another preferred embodiment, the elongated probe comprises at its distal end an exposed shaped member connected to a wire end. Preferably, the shaped member has in front an American football shape or a bullet shape, which is especially useful for endonasal procedures.

Preferably, the overall outside diameter of the electrosurgical electrode of the invention is 1 mm or less, and it has an overall length, measured from the connector, of at least about 475 mm, preferably, about 600 mm for certain procedures, especially spinal procedures, but for treating endonasal tissues that can be reached with a shorter electrode a length of at least about 150 mm is preferred. A longer length of at least about 280 mm is generally preferred for most procedures. For such procedures, a maximum diameter of about 0.06 mm can be used.

By "proximal" is meant the end closest to the connector, and by "distal" is meant the end furthest from the connector.

The construction of the invention will provide important benefits for all MIS arthroscopic or endoscopic procedures and in many cases enables the efficient delivery of radiofrequency (RF) energy technology for controlled precise tissue cutting, absorption and other tissue effects and in a safe manner. It is cost effective and considerably less expensive than other surgical modalities such as lasers where the novel electrode configuration may be of importance, as well as for general electrosurgical procedures where the volumetric reduction of tissue or ablation of tissue that is hard to reach with the known electrodes is desirable. Examples of particular procedures for which the electrosurgical electrode of the invention is particularly suitable is spinal disc reduction and endonasal procedures.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals designating the same or similar elements.

BRIEF DESCRIPTION OF THE DRAWINGS

In the drawings:

FIG. 1 is a schematic view of one form of an electrosurgical probe according to the invention shown coiled to emphasize its flexibility and also connected to electrosurgical apparatus;

FIG. 2 is a side and partially cross-sectional view of the straightened electrosurgical probe shown in FIG. 1 with its attached connector;

FIG. 3 is an enlarged cross-sectional view of the working end of the probe of FIG. 2;

DETAILED DESCRIPTION OF PREFERRED EMBODIMENTS

Figure 5:
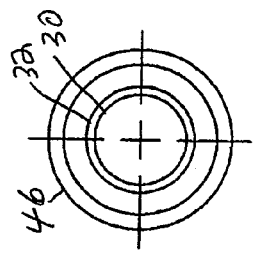
FIG. 5 is an end view of the working end of the probe of FIG. 4.

The reader is directed to the referenced prior patents for a more detailed description of electrosurgical procedures and principles of operation which will assist in understanding the invention described in the present application.

In the present application, FIG. 1 is a generally schematic view of one form of electrosurgical electrode 10 in accordance with the invention shown connected by way of engagable connectors 12, 14 and a cable 16 to a conventional electrosurgical apparatus 18. FIG. 2 shows just the electrode part with in this case a female connector 12.

The connector 12 construction is a hollow insulating member made of an autoclavable plastic with outer grooves or knurls 20 for easy manipulation by the fingers of a user, and containing at its right end a reduced diameter section 22. Inside a bore 24 extends a hollow metal, e.g., of brass, female receptacle 26 which is fully surrounded by the insulating section 22, and is actually recessed 27 a short distance to prevent accidental contact with the user. The female receptacle 26 narrows down to a thin tube 28 into which is mounted the bare end of a metal wire 30 thereby forming a good electrical connection between the metal receptacle 26 and the wire 30. The connection between the latter can be for example by welding or brazing. Except for that welded or brazed connection, the remainder of the wire 30 is surrounded by a thin insulating coating or sheath 32 of a flexible autoclavable plastic such as Teflon. The entire length of the wire 30 is sheathed in this insulating sheath 32 except for a small section 34 at the distal end of the wire which is left bare and electrically exposed. That bare end 34, shown enlarged in FIG. 3, is the working end of this form of the electrode. The female connector 12 is permanently attached to the wire 30. The wire 30 is preferably made of tungsten though other electrically conductive metals that when thin are flexible can be used such as stainless steel and brass. The exposed bare end 34 is equal to or less than about 1 mm, and can be as small as 0.125 mm. The coating adds only about 0.15 mm. For certain procedures, the end 35 should be blunt so it will more easily pass through a cannula, especially a bent cannula.

For its intended use, the elongated electrode 10 comprises a thin highly flexible insulated wire that is sufficiently thin and flexible, but sufficiently stiff, that it can be used with a flexible steerable endoscope or a miniature micro endoscope and in addition can be snaked down or threaded up into a vein to reach, e.g., leg lesions. It has sufficient resilience that, if bent, it will spring back to its initial position. For these applications, the overall diameter of the sheathed wire must be about 1 mm or less, and it must have an overall length, measured from the connector 12, of at least about 475 mm, preferably, about 600 mm. Thus, a miniature micro endoscope whose channel is typically less than about 3 mm can accommodate the wire, and its flexibility allows it to be used with flexible steerable endoscopes, flexible cannulas, and flexible scopes to access areas of the body internally. Its very long length enables the working end 34 to reach tissue at body locations that heretofore were only reachable by means of a laser fiber or traditional surgery.

One form of the electrode of the invention is especially important for spinal surgery, for example, targeted treatment of epidural scar tissue, adhesions and other pathology, or for precise intradiscal shrinkage or ablation. Combined with a miniature micro endoscope, in turn combining imaging optics and an instrument channel with an overall diameter below 3 mm, access and visualization of the epidural space is now a viable option.

A further advantage is obtained when the electrode of the invention is used with electrosurgical apparatus capable of generating RF electrosurgical currents at frequencies of about 4 MHz. The monopolar electrode wire thus enables the efficient delivery of RF energy and is uniquely suited for spinal procedures, such as myeioscopy or endoscopic epiduraplasty, due to the controlled precise tissue absorption and versatile tissue effects and safety it affords. The resultant technology is cost effective and considerably less expensive then other surgical modalities such as lasers, and offers the further advantage that it delivers lower tissue temperature profiles. Moreover, it allows more easily the extension of RF electrosurgical currents to minimal and micro invasive surgical procedures. Minimal and micro surgical procedures typically result in reduced pain and scarring, shorter recovery time and increased effectiveness compared to traditional surgical procedures. Most of the pain associated with traditional surgery procedures results from the cutting of layers of skin and muscle tissue, which also delays healing and generates high levels of pain. An example of suitable electrosurgical apparatus is the Model SURGITRON Dual-Frequency electrosurgical unit manufactured by and available from Ellman International, Inc. of Oceanside, N.Y.

As indicated in FIG. 1, the female connector 12 is connectable to its male counterpart 14, which comprises also a hollow insulating member 39 made of an autoclavable plastic with outer grooves or knurls 40 and contains on a bore 42 inside a recessed electrically conductive male plug 44 which is internally connected to the cable 16 that can be plugged into the electrosurgical apparatus 18. The configuration is such that when the two connectors 12, 14 are engaged, the male contact 44 will engage the female receptacle 26 whereupon the cable 16 is connected to the wire electrode 30. The overall length of the engaged connectors is about 60–80 mm, each being about one-half the length. The direct connection of the wire electrode to the novel connector 12, which is a departure from traditional electrosurgery electrode handpieces, has the important advantage that the engaged connectors 12, 14 can function as a finger connector and is simply maneuvered and manipulated with the fingertips of the user, typically the index finger and thumb fingertips. Since the entire electrode 10 with its attached connector as well as the connector 14 are autoclavable, i.e., sterilizable, while maintaining the sterile field at the patient's site, the surgeon when desired can with one hand disconnect or connect the sterile connectors 12, 14 and reconnect to the free female connector 12 another electrode, say for a different cutting, shrinking or coagulating function.

It will also be appreciated that the arrangement of the male and female parts of the connectors can be reversed, but in the manner illustrated certain standard practices are followed allowing other male oriented connectors to be connected to the female connector 12.

While the blunt wire end 35 illustrated is the most versatile, it may be desirable to provide a small ball at the distal end for easier threading through a vein.

A further important application for the electrosurgical electrode of the invention is in the treatment more specifically for endoscopic endonasal surgery with RF electrosurgical currents, preferably at about 34 MHz. In the past, such sinus and nasal procedures could be done only with a laser fiber. The electrosurgical electrode of the invention can easily accomplish the same ablative, vaporizing, and debulking of diseased tissue within the nasal cavity, but with the benefits described above. For such applications, we prefer a sheathed fiber that that comprises an insulatingly coated thin wire of less than about 1 mm in diameter, provided with a generally American football-shaped electrically-conductive member affixed to the end of the wire to form the active end. The football shape allows the operating surgeon to traverse or sweep the tissue area to be treated with the smooth sides of the active end which may be desirable for ablative, vaporizing, and debulking of diseased tissue. A bullet shape, simulating one-half of a football may also be suitable.

Figure 7:
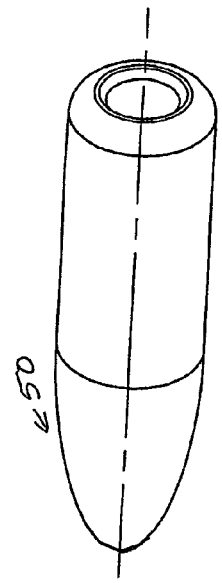
FIG. 7 is a perspective view of the working end of the probe of FIG. 6.
Figure 4:
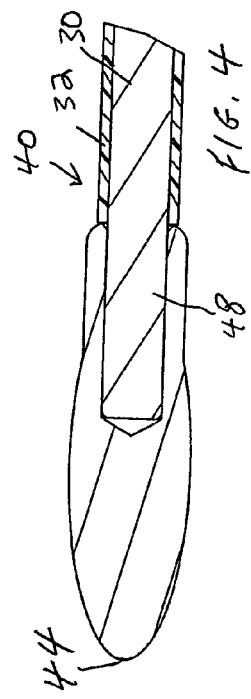
FIG. 4 is an enlarged cross-sectional view of the working end of the probe to which a football-shaped member has been attached.
Figure 6:
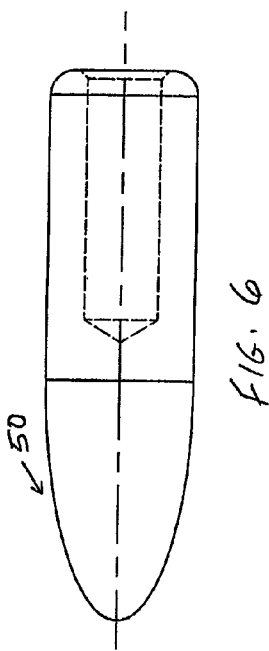
FIG. 6 is an enlarged side view of the working end of the probe to which a bullet-shaped member has been attached.
Figure 8:
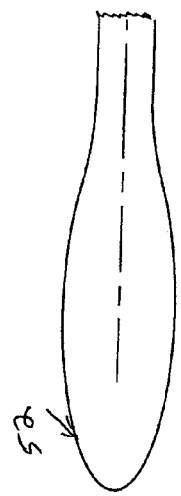
FIG. 8 is an enlarged side view of the working end of the probe to which another shaped member has been attached.

FIGS. 4 and 8 illustrate, respectively, active ends having football and bullet shapes. In FIG. 4, the sheathed conductive fiber is indicated by 40, and the attached exposed football-shaped end is indicated by 42. The football shape, which in its forward section in cross-section resembles an ellipse, is preferred because of its smooth sides all around and the tapered un-pointed distal end 44 which makes the electrode easier to move around in the nasal tissue and provides good visualization of the active tissue site. The OD of the ellipse at its maximum diameter 46 is preferably about 0.5–0.75 mm. One-half of the major axis of the ellipse is preferably about 1–1.5 mm. Its overall length is preferably about 2–4 mm. It may be attached to the wire end by, for example, solder or an electrically-conductive adhesive. The bullet shape 50 illustrated in FIGS. 6 and 7 has a similar front end configuration and will also prove acceptable for many procedures. FIG. 8 shows another useful shape with similar properties.

Figure 9:
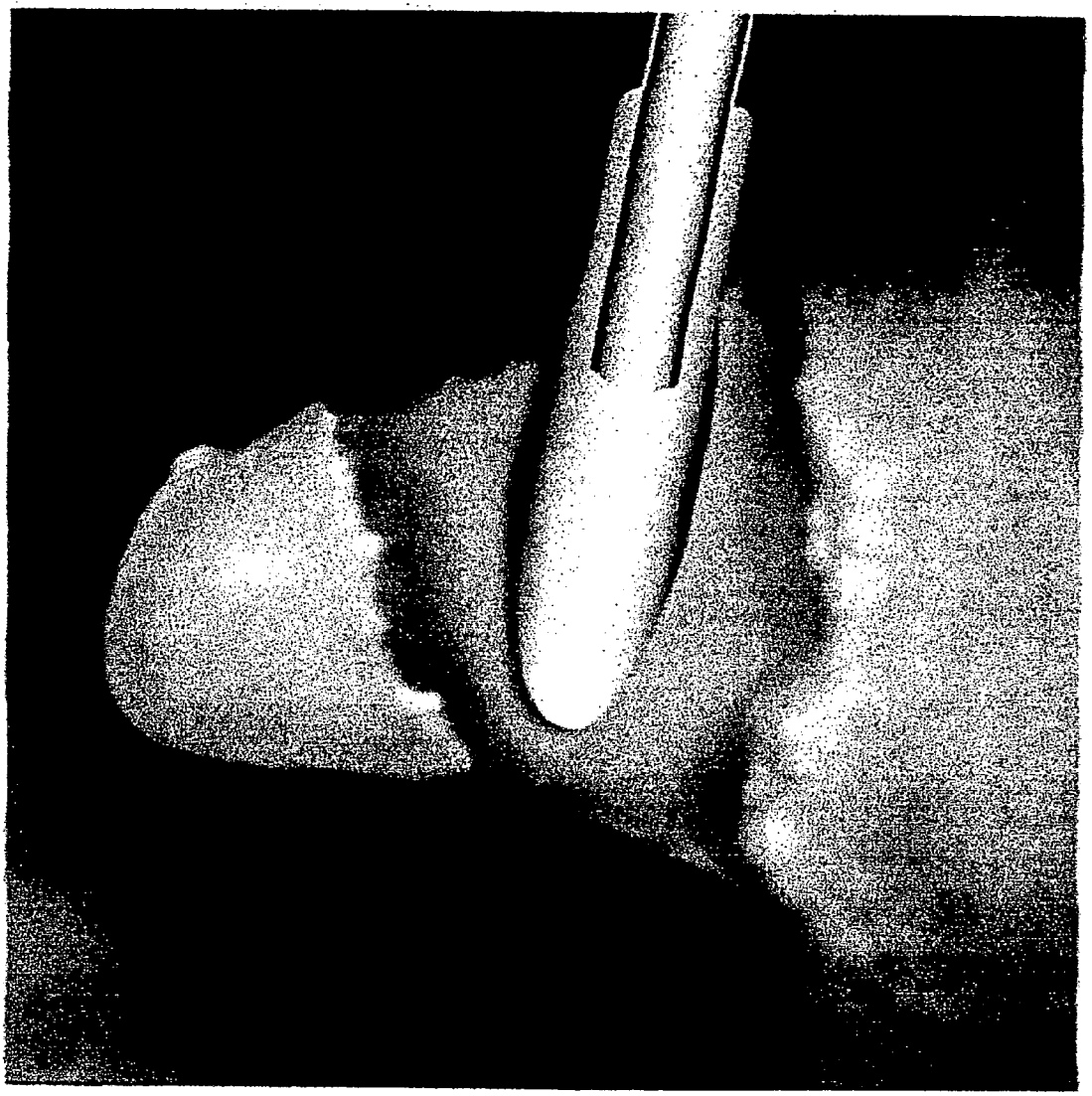
FIG. 9 is a schematic view illustrating one possible procedural use of an electrosurgical electrode according to the invention.

FIG. 9 illustrates schematically the electrode of the invention of FIG. 4 present in the sinus region of a patient via an endonasal scope. The view shown is the endoscopic depiction of the endonasal electrode of the invention with the football tip resecting the septal spur. This procedure previously could only be accomplished with a laser, with the possible disadvantages that the laser can produce a high degree of char and there may be delayed healing and post operative complications as a result. The RF electrosurgical electrode of the invention preserves the tissue and will enhance the healing process. Endoscopes that can be used are available commercially and such endoscopes and such types of procedures using lasers are described at length in "Functional Endoscopic Endonasal Surgery", by Hopf and Hopf, published 2001 by Endo-Press of Tuttlingen, Germany, summarized at Pgs. 6–8.

In this description, by "elongated" or "longitudinal" is meant parallel to the long axis of the electrode (horizontal in FIG. 2).

Once the surgeon has positioned the working end 34 of the electrode with respect to the tissue to be operated on, he or she then activates the electrosurgical apparatus 18 causing a discharge of unipolar currents between a ground plate (not shown) and the bare electrode end 34 capable of causing excision or ablation or shrinkage of tissue or cauterization of a blood vessel in the usual way. As with the embodiments of the prior patents, the insulating coating on the electrode 10 will prevent accidental touching of any conductive members or patient tissue by the electrode sides, so that the unipolar discharge is localized to the region surrounding the working end 34.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical monopolar probe for treating tissue, comprising:
   (a) an elongated member having a major longitudinal axis and having a proximal first end and a distal second end comprising an active electrode, the elongated member comprising a long thin flexible wire covered with an insulator except for a bare active second end,
   (b) said elongated member having sufficient resilience such that when bent will spring back to its unbent position and being sufficiently thin and flexible such that it can be passed through a straight or bent cannula or tissue having an inside diameter equal to or less than about 3 mm,
   (c) an insulated connector attached to and fully surrounding the first end so as to allow the passage of electrosurgical currents between its proximal and distal ends when the connector is connected to a source of electrosurgical currents but will prevent accidental electrical contact of the first end with the tissue,
   (d) wherein electrosurgical currents applied to the proximal end when an electrosurgical voltage is applied thereto will reach and activate the active end.

2. The electrosurgical probe as claimed in claim 1, wherein the outside diameter of the insulated wire is equal to or less than about 1 mm.

3. The electrosurgical probe as claimed in claim 2, wherein the probe has an overall length, measured from the connector, of at least about 475 mm.

4. The electrosurgical probe as claimed in claim 1, wherein the bare second end has a forward section which in cross-section resembles an ellipse to form a football or bullet shape.

5. The electrosurgical probe as claimed in claim 4, wherein the maximum diameter of the bare active second end of the electrode is about 0.5–0.75 mm.

6. The electrosurgical probe as claimed in claim 5, wherein the length of the bare active second end of the electrode is about 2.5–4 mm.

7. A surgical procedure using a mini-endoscope having a canal of about 4 mm or less, comprising the steps:
   A) positioning the viewing end of the endoscope at a surgical site, B) inserting into the canal an electrosurgical electrode probe comprising:
  (a) an elongated member having a major longitudinal axis and having a proximal first end and a distal second end comprising an active electrode, the elongated member comprising a long thin flexible wire covered with an insulator except for a bare active second end,
  (b) said elongated member having sufficient resilience such that when bent will spring back to its unbent position and being sufficiently thin and flexible such that it can be passed through the canal when straight or bent,
  (c) an insulated connector attached to and fully surrounding the first end so as to allow the passage of electrosurgical currents between its proximal and distal ends when the connector is connected to a source of electrosurgical currents but will prevent accidental electrical contact of the first end with tissue at the surgical site,
C) supplying monopolar electrosurgical currents to the proximal end to reach and activate the active end, and applying the active end to tissue at the surgical site to modulate the tissue.

8. The surgical procedure of claim 7, wherein the supplied electrosurgical currents are at a frequency of about 4 MHz.

9. The surgical procedure of claim 7, wherein the procedure is spinal surgery.

10. The surgical procedure of claim 7, wherein the procedure is an endonasal procedure.

* * * * *